United States Patent [19]

Danziger et al.

[11] 4,148,792
[45] Apr. 10, 1979

[54] PURIFICATION OF CAPROLACTAM

[75] Inventors: Harry Danziger; Otto Immel; Bernd-Ulrich Kaiser, all of Krefeld, Fed. Rep. of Germany; Guido Rampart, Ekeren, Belgium; Hans-Helmut Schwarz, Krefeld, Fed. Rep. of Germany

[73] Assignee: Bayer Aktiengesellschaft, Leverkusen, Fed. Rep. of Germany

[21] Appl. No.: 915,732

[22] Filed: Jun. 15, 1978

Related U.S. Application Data

[63] Continuation of Ser. No. 831,789, Sep. 9, 1977, abandoned.

[30] Foreign Application Priority Data

Sep. 15, 1976 [DE] Fed. Rep. of Germany ....... 2641478

[51] Int. Cl.² ........................................... C07D 201/16
[52] U.S. Cl. .............................................. 260/239.3 A
[58] Field of Search ................................. 260/239.3 A

[56] References Cited

U.S. PATENT DOCUMENTS

| 2,752,336 | 6/1956 | Boon et al. | 260/239.3 A |
| 3,154,540 | 10/1964 | Beer et al. | 260/239.3 A |
| 3,476,744 | 11/1969 | Berther et al. | 260/239.3 A |
| 3,882,102 | 5/1975 | Immel et al. | 260/239.3 A |

*Primary Examiner*—Natalie Trousof
*Assistant Examiner*—Robert T. Bond
*Attorney, Agent, or Firm*—Connolly and Hutz

[57] ABSTRACT

A process for the purification of ε-caprolactam, wherein ε-caprolactam is treated with potassium permanganate in the presence of from 0.01 to 5% by weight of water, based on caprolactam, and subsequently crystallized from toluene, benzene, ethylbenzene or xylene.

4 Claims, No Drawings

PURIFICATION OF CAPROLACTAM

This application is a continuation of application Ser. No. 831,789 filed Sept. 9,1977 now abandoned.

For purification and in order to improve its colour, ε-caprolactam has been treated with potassium permanganate. In general, the permanganate is added in the form of an aqueous solution to an aqueous solution of the caprolactam so that a dilute aqueous solution is present during purification by oxidation. Considerable importance is attached to the presence of water in an adequate quantity. Water-soluble lactams have even been added during the treatment of water-insoluble lactams in order to obtain an aqueous medium, However, the treatment of dilute aqueous caprolactam solutions with potassium permanganate is accompanied by the appearance of a yellow colour which cannot be eliminated by crystallisation from the solvents mentioned. Colour numbers of the order of 250 are generally obtained. This yellowing is avoided by the process of the invention, i.e. a process for the purification of ε-caprolactam, wherein ε-caprolactam is treated with potassium permanganate in the presence of from 0.01 to 5% by weight of water, based on caprolactam and subsequently crystallised from toluene, benzene, ethyl benzene or xylene. In general, the caprolactam to be purified, which may already have been subjected to an extraction step and/or a crystallisation step, is first dehydrated, after which potassium permanganate is added, preferably in the form of a concentrated aqueous solution, the water content of the mixture being from 0.01 to 5% by weight and the quantity of potassium permanganate being adjusted so that it is completely reduced in 5 minutes at a temperature of 80° C. In general, quantities of from 0.05 to 0.1% by weight, based on the caprolactam, are required for this purpose. On completion of the reaction, one of the solvents benzene, ethylbenzene and xylene, but preferably toluene, is added, the ε-caprolactam is dissolved therein and crystallised. The solid product which has crystallised is, generally, pure enough after washing and drying for a subsequent polymerisation reaction. It has a solidification point above 69° C, a colour number around 5, a content of volatile bases of 0.3 mEq/kg (milliequivalents per kilogram) or less, a UV number of 95 and a permanganate number of >40,000. In particular, it is completely colourless, as indicated by the colour number.

EXAMPLE 1

200 g of caprolactam crystals, obtained from crude caprolactam of the gaseous-phase re-arrangement of cyclohexanone oxime by extraction with toluene and crystallisation from toluene, were melted and then stirred for 30 minutes at 80° C.with 2 g of 10% aqueous potassium permanganate solution. 86 g of toluene were then added, and the resulting solution was then filtered and crystallised by gradual cooling to 20° C. The crystal sludge obtained was filtered, made into a pulp with toluene and centrifuged. The characteristics of the ε-caprolactam obtained after drying were as follows:

| | |
|---|---|
| Solidification point | 69.10° C. |
| Hazen colour number | 5 |
| Content of volatile bases (removable with NaOH; amines) | 0.15 mEq |
| UV number | 95 |
| Permanganate number | >40,000 |

EXAMPLE 2

200 g of caprolactam crystals, obtained by crystallisation of ε-caprolactam obtained by decomposition of polyamide, with the following characteristics:

| | |
|---|---|
| Solidification point | 69.00° C. |
| Colour number | 200 |
| volatile bases | 2.0 mEq/kg |
| UV number | 10 |
| Permanganate number | 600 | were treated and worked up described in Example 1. Thereafter the characteristics of the resulting ε-caprolactam were as follows:

| | |
|---|---|
| Solidification point | 69.10° C. |
| Colour number | 5 |
| Volatile bases | 0.25 mEq/kg |
| UV number | 95 |
| Permanganate number | >40,000 |

EXAMPLE 3

Caprolactam produced by Beckmann's rearrangement was extracted with toluene. 2000 g of toluene/caprolactam extract (80% by weight of toluene) were concentrated to 600 g. This solution was stirred for 30 minutes at 80° C.with 1g of 10% aqueous potassium permanganate solution. Further working up in accordance with Example 1 produced the following characteristics of the ε-caprolactam obtained:

| | |
|---|---|
| Solidification point | 69.10° C. |
| Colour number | 5 |
| Volatile bases | 0.10 mEq/kg |
| UV number | 98 |
| Permanganate number | >40,000 |

EXAMPLE 4

100 ppm of dehydrogenated caprolactam were added to 200 g of pure caprolactam. The mixture had a permanganate number of 1000. It was treated and worked up in accordance with Example 1. The following characteristics were obtained for the resulting ε-caprolactam.

| | |
|---|---|
| Solidification point | 69.10° C. |
| Colour number | 5 |
| Volatile bases | 0.15 mEq/kg |
| UV number | 98 |
| Permanganate number | >40,000 |

COMPARISON EXAMPLE 1

In comparison Example 1, 200 g of caprolactam from the crude crystallisation stage of the catalytic rearrangement process were dissolved in 298 g of water and then stirred for 30 minutes at 80° C.with 2 g of 10% aqueous potassium permanganate solution. The caprolactam solution was then filtered and distilled until free from water. 86 g of toluene were added to the caprolactam thus isolated, followed by slow cooling from 60° C. to 20° C. The crystal sludge was then further processed in the same way as described in Example 1. The following characteristics of the caprolactam were obtained:

| Solidification point | 69.00° C. |
|---|---|
| Color number | 250 |

COMPARISON EXAMPLE 2

The procedure was as in Comparison Example 1, including the step of distillation to remove water. Then 86 g of toluene and 2 g of active carbon were added to the anhydrous caprolactam, followed by stirring for 10 min. at 60° C. The active carbon was then filtered off and the caprolactam crystallised out of the filtrate. The crystal sludge was worked up in the same way as in Example 1. Caprolactam with the following characteristics was obtained:

| Solidification Point | 69.10° C. |
|---|---|
| Colour number | 50 |

COMPARISON EXAMPLE 3

100 ppm of dehydrated lactam were added to 200 g of pure caprolactam, followed by oxidation and purification in accordance with Comparison Example 1 for comparison with Example 4. Caprolactam with the following characteristics was obtained:

| Solidification point | 69.06° C. |
|---|---|
| Colour number | 10 |
| Volatile bases | 0.3 mEq/kg |
| UV numbers | 86 |
| Permanganate number | 30,000 |

What we claim is:
1. A process for the purification of $\epsilon$-caprolactam obtained from crude caprolactam of the gaseous-phase rearrangement of cyclohexanone oxime or produced by Beckmann's rearrangement which comprises treating said crude caprolactam with potassium permanganate in the presence of from 0.01 to 5% by weight of water, based on the $\epsilon$-caprolactam, and subsequently crystallizing $\epsilon$-caprolactam from toluene, benzene, ethylbenzene or xylene.
2. A process as claimed in claim 1, wherein the $\epsilon$-caprolactam is crystallised from toluene.
3. A process as claimed in claim 1, wherein from 0.05 to 0.1% by weight of water, based on the $\epsilon$-caprolactam is present.
4. A process as claimed in any of claim 1, wherein the quantity of potassium permanganate is controlled so that it is completely reduced in 5 minutes at a temperature of 80° C.

* * * * *